United States Patent [19]

Schiraldi et al.

[11] Patent Number: 4,992,259

[45] Date of Patent: Feb. 12, 1991

[54] STABLE ORAL COMPOSITION OF ZINC

[75] Inventors: Michael T. Schiraldi, East Brunswick; Robert K. Denton, Jr., Trenton, both of N.J.

[73] Assignee: Johnson & Johnson Consumer Products, Inc., New Brunswick, N.J.

[21] Appl. No.: 460,442

[22] Filed: Jan. 3, 1990

[51] Int. Cl.$^5$ .................. A61K 7/16; A61K 33/30
[52] U.S. Cl. .................. 424/49; 424/55; 424/641; 424/642; 424/643
[58] Field of Search .................. 424/49, 55, 641, 642, 424/643

[56] References Cited

U.S. PATENT DOCUMENTS

| | | | |
|---|---|---|---|
| 4,022,880 | 5/1977 | Vinson | 424/49 |
| 4,100,269 | 7/1978 | Pader | 424/642 |
| 4,138,477 | 2/1979 | Gaffar | 424/52 |
| 4,144,323 | 3/1979 | Lamberti | 424/54 |
| 4,211,341 | 7/1980 | Weyn | 222/94 |
| 4,296,096 | 10/1981 | Pierce | 424/49 |
| 4,339,432 | 7/1982 | Ritchey | 424/54 |
| 4,425,325 | 1/1984 | Ritchey | 424/54 |
| 4,568,540 | 2/1986 | Asano | 424/52 |
| 4,645,662 | 2/1987 | Nakashima et al. | 424/49 |
| 4,664,906 | 5/1987 | Sipos | 424/49 |
| 4,765,984 | 8/1988 | Vellekoop et al. | 424/49 |

FOREIGN PATENT DOCUMENTS 2604625 4/1988 France .

Primary Examiner—Shep K. Rose
Attorney, Agent, or Firm—Joseph J. Brindisi

[57] ABSTRACT

A stable and clear aqueous solution of zinc salt useful as a mouthrinse and a gel dentifrice. In a preferred embodiment the aqueous solution comprises zinc chloride codissolved with a complexing agent of sodium gluconate, in a naturally derived anionic polymer of sodium carboxymethylcellulose. This solution is advantageous because it maintains clarity and chemical stability in temperatures of from about 4° to about 50° C. and may be alcohol-free. The anionic polymer acts as a buffer to provide a solution with a pH in a desirable range of from about 5.7 to about 6.5, which limits astringency and tartness.

15 Claims, No Drawings

STABLE ORAL COMPOSITION OF ZINC

FIELD OF THE INVENTION

The present invention relates to a stable and clear aqueous composition and a process for making and using the composition. In particular, the present invention relates to a stable and clear aqueous composition comprising a zinc compound which is useful as a mouth rinse and gel dentifrice.

BACKGROUND OF THE INVENTION

The literature is replete with the use of zinc compounds as a source for a physiologically active zinc ion in mouthwashes, rinses, toothpastes and dentifrices. Zinc has been used most often for its ability to meliorate oral malodor (bad breath). Additionally, zinc compounds have been utilized as astringent-desensitizing agents. It has also been proposed by those skilled in the art that the zinc ion has anticalculus and antiplaque properties. The attempted formulation of stable, biologically active zinc containing products has, however, met with problems.

Highly ionized and soluble zinc salts, such as zinc chloride, provide the best source of zinc ions having the greatest bioavailability. However, zinc chloride in aqueous solution over time tends to form oxychlorides and zinc hydroxides. These byproducts all have low solubility and result in cloudy, unaesthetic solutions. Therefore, in an attempt to maintain clear, stable solutions of zinc compounds, the following approaches have been taken by those skilled in this art.

The pH of the conventional zinc chloride solution has been lowered to less than 4.5 through the use of mineral or organic acid buffers in an attempt to provide a clear, stable solution. This technique suffers, however, from the fact that the final products have severe astringency and an unacceptably sour taste.

The use of certain zinc salts such as zinc phenolsulfonate, as disclosed in U.S. Pat. No. 4,022,880, or carboxymethylsuccinate, as disclosed in U.S. Pat. No. 4,144,323, which tend to be stable at a higher pH than other zinc salts, has also been proposed.

Sparingly soluble salts such as zinc citrate, have been used to slow down the release of zinc ions thereby reducing astringency and presumably providing a sustained level of in-vivo activity and increased formula stability.

The use of various complexing agents such as sodium gluconate, as disclosed in U.S. Pat. No. 4,568,540, glycine, as disclosed in U.S. Pat. Nos. 4,339,432 and 4,425,325, sodium citrate, citric acid, and the like, have been proposed in an attempt to produce relatively stable solutions of zinc chloride.

U.S. Pat. No. 4,568,540 discloses an oral hygiene composition containing a fluoride salt, zinc salt, a buffering agent such as sodium gluconate and a vehicle, having a pH of from about 3.5 to 6.0. Opacified dentifrice formulations are disclosed which contain non-ionic polymer binders such as hydroxyethylcellulose polymers.

The reaction or interaction of zinc compounds of varying solubility with anionic polymers containing carboxylic, sulphonic and/or phosphonic acid functionalities is disclosed in U.S. Pat. No. 4,138,477.

U.S. Pat. No. 4,664,906 discloses oral compositions which exhibit antimicrobial activity containing hexedine and a zinc compound. Opacified gel dentifrices are disclosed which contain sodium gluconate and a non-ionic binder such as hydroxyethyl cellulose.

All of the products derived from these approaches ameliorate oral malodor with varying degrees of effectiveness. The mechanism that has been most often advanced by those skilled in the art for this effect is the ability of the free $Zn^{+2}$ to form insoluble salts with nucleophilic compounds, i.e., valeric acid, skatole, indole-3-acetic acid, hydrogen sulfide, mercaptans, and the like, which compounds are typically the cause of oral malodor. All of these substances are respiratory byproducts of the gram-negative (putrefactive) bacteria that are found in the mouth. Once these salts have been formed, they are expectorated with the mouth rinse at once or swallowed with the saliva.

Unfortunately, of the methods noted above, only the lowering of the pH of the zinc chloride solution to less than 4.5 through the use of mineral or organic acid buffers provides well ionized and readily bioavailable zinc ions in a clear, stable solution. This method is unacceptable however, as detailed above.

Some of the weakly complexed zinc compounds resulting from the use of various complexing agents, as noted above, may provide readily available zinc ions, but the formulations suffer from being unstable over time. The stable, strongly complexed or sparingly soluble zinc compounds have only a short term effect against the malodorant chemicals. Once the initial effect has taken place, the remaining unreacted zinc salt or complex is expectorated leaving little or no residual odor control or bacteriostatic effect.

The importance of readily bioavailable zinc is that the cation, once it has entered the oral environment, rapidly adsorbs onto proteins of the oral mucosa and dental pellicle, while simultaneously reacting with oral malodorants. The zinc which does not react immediately will release from the proteinaceous substrate over time, extending its effect significantly. There is also evidence that the retained zinc is bacteriostatic towards gram-negative microbes. The art, however, lacks an aesthetically acceptable composition capable of providing a truly effective amount of bioavailable zinc ions.

U.S. Pat. No. 4,138,477 discloses an oral composition containing a zinc-polymer combination. Suitable zinc compounds include zinc chloride and zinc gluconate. Optionally, the complex can include a dental vehicle containing liquids comprising water and/or a humectant, and solids, comprising carboxymethyl cellulose as a gelling agent. The preferred anionic polymer disclosed is Gantrez TM, a brand name of a copolymer of maleic anhydride and vinyl methyl ether. This compound is hydrolyzed to form a dicarboxylic acid; which is then complexed with various zinc salts, preferably zinc chloride. The polymer is used in a 4:1 weight ratio with zinc salt, and when adjusted for average carboxyl substitution the zinc to carboxyl group ratio is 1:3. Each zinc ion is capable of being o strongly complexed with the Gantrez TM and most likely renders the zinc ion functionally unavailable and therapeutically useless.

The zinc/GantrezT TM combination described above has an unacceptably low astringency. Although this lack of astringency may be desirable from an organoleptic viewpoint, it is subjective evidence for the lack of bioavailable zinc ions. Astringency is a side-effect of the zinc ion forming complexes with proteins of the oral mucosa. Attenuation of this effect probably indicates a reduced quantity of available zinc ions. A relatively greater astringency on the other hand would suggest the presence of more available zinc.

U.S. Pat. No. 4,138,477 discloses, at column 2, lines 16–47, that only 53% of the zinc present in the formulations, as measured by equilibrium dialysis, was released after 24 hours, with none being released after 10 minutes or after 1 hour. In the presence of saliva only 7% of the zinc was detected after 24 hours.

Moreover, a release of zinc from the anionic polymer is not induced by exposing the anionic polymer solution to the presence of calcium ions. The relatively more electropositive calcium would be expected to displace the zinc from the polymer, especially in the case where the ionic balance is tenuous. Thus, for at least these reasons it is believed that this zinc/Gantrez TM M complex is very strong and most likely renders the zinc ion functionally unavailable.

The art, therefore, lacks a stable and clear aqueous composition of zinc salt, which is truly effective as a mouthrinse and gel dentifrice. A composition having these properties would provide an improved agent for combating the problems of oral malodor, plaque, calculus and periodontal disease.

It is therefore an object of the present invention to provide a stable and clear aqueous composition comprising a zinc compound which provides a source of bioavailable zinc ions from a readily aqueous soluble zinc salt and is useful as a mouth rinse and gel dentifrice for the control of malodor and prevention of calculus.

It is also an object of the present invention to provide an aqueous zinc containing oral formulation having a pH suitably close to oral pH to limit astringency and tartness.

Other objects and aspects of the present invention will become apparent to those skilled in the art from the following description and the appended claims.

SUMMARY OF THE INVENTION

The foregoing objects have now been accomplished in accordance with the compositions, processes and methods of the present invention.

In accordance with the purposes of the invention as embodied and fully described herein, the invention comprises a stable and clear aqueous composition of zinc salt which includes a complexing agent and an anionic polymer, which is useful as a mouthrinse and gel dentifrice. The aqueous composition has a pH in the range of from about 5.7 to about 6.5. These objects are also achieved by a stable and clear aqueous solution of zinc salt, which is preferably alcohol-free.

The present invention further comprises a stable and clear aqueous composition of a zinc salt including a pharmaceutically acceptable zinc salt codissolved with a complexing agent selected from the group consisting of sodium gluconate, maleic acid, aspartic acid, gluconic acid, succinic acid, glucuronic acid, sodium glutamate, fumaric acid and mixtures thereof, in a naturally derived anionic polymer of sodium carboxymethylcellulose (hereafter "NaCMC") or sodium alginate, the composition having a pH of from about 5.7 to about 6.5.

As embodied and broadly described herein the present invention comprises a method for meliorating oral malodor which includes applying the zinc composition of the present invention to the oral cavity. In further preferred embodiments the method comprises applying the zinc composition of the present invention to the oral cavity, wherein an effective quantity of free $Zn^{+2}$ ions are released instantaneously from the composition and the composition absorbs onto the oral mucosa and dental pellicle wherein an effective quantity of free $Zn^{+2}$ ions are released gradually from the composition by an ion-exchange mechanism with salivary $Ca^{+2}$.

As embodied and broadly described herein the present invention comprises a process for preparing a stable and clear aqueous composition of a zinc salt including the steps of:

(a) dissolving sodium gluconate in water with stirring forming an aqueous gluconate solution;

(b) adding slowly sodium carboxymethylcellulose to the aqueous gluconate solution with stirring until substantially all the carboxymethylcellulose grains are dissolved;

(c) thereafter dissolving zinc chloride in the aqueous gluconate carboxymethylcellulose solution with stirring and (d) after mixing allowing the resultant solution to sit to allow formation of the zinc/gluconate/carboxymethylcellulose complex.

DETAILED DESCRIPTION OF THE PREFERRED EMBODIMENTS

The present invention relates to an aqueous solution of zinc salt, codissolved with a complexing agent and a naturally derived, anionic polymer. The aqueous solution may be utilized to manufacture mouthwashes and mouthrinses (alcoholic and preferably, alcohol-free) and gel dentifrices.

An advantage of the present invention is that the solutions prepared by this technique are clear and aesthetically pleasing. They have been shown to maintain clarity and chemical stability at both a low temperature of 4° C. and a high temperature of 50° C. in accelerated aging tests for over eight weeks. An additional advantage is that the anionic polymer employed, such as NaCMC and NaAlginate, acts as a buffer, providing solutions with a pH in the range of from about 5.7 to about 6.5. The pH of the solution therefore remains stable. Zinc ions not stabilized by the complexing agent are combined with the anionic polymer. Any free zinc which may give rise to cloudiness via the formation of zinc hydroxide or oxychloride is believed to be taken up by the anionic polymer, maintaining the solution clarity and steadying the pH. Upon use significant quantities of free $Zn^{+2}$ are released from the complexing agent and adsorb onto the oral mucosa and dental pellicle. Further, the anionic polymer/zinc/gluconate combination complex is believed to adsorb onto the mucosa and pellicle where the zinc ions are gradually released by an ion-exchange mechanism with salivary $Ca^{+2}$. Theoretically this gradual release helps sustain the beneficial effects due to the presence of zinc ions over time.

Any pharmaceutically acceptable zinc salt is suitable in accordance with the present invention. The term "pharmaceutically acceptable" with reference to zinc compounds as used herein refers to any salt of zinc that is safe and organoleptically tolerable in the oral cavity, and has no significant known side effects, either systemically or topically. Examples of preferred zinc salts include zinc sulfate, zinc acetate, zinc thiocyanate, zinc lactate, zinc salicylate and zinc chloride. The preferred salts have sufficient solubility at or about 37° C. to dissociate into bioavailable zinc ions ($Zn^{+2}$), and provide the equivalent of about one gram of zinc per 100 ml of water. Zinc chloride is the most preferred zinc salt for purposes of the present invention.

The buffering/complexing agents of the present invention are preferably organic acids and organic acid salts which prevent the precipitation of the zinc ion. Sodium gluconate preferably present in an amount of from about 0.01 to about 10.0% and more preferably from about 0.05 to about 5.0%, is one suitable buffer. Other acceptable organic acids/salts which can be used include maleic acid, aspartic acid, gluconic acid, succinic acid, glucuronic acid, sodium glutamate and fumaric acid.

In contrast, organic acids which are stronger complexing/chelating agents than those of the present invention are not acceptable. Examples of unacceptable complexing agents include tricarboxylic acids such as citric acid, gallic acid, tannic acid and strong chelating compounds like EDTA (calcium), EDTA (sodium) and EDTA.

The anionic polymers useful for this invention are water soluble, and capable of complexing via a carboxylic moiety with the polyvalent zinc cation. Examples of useful anionic polymers are specifically (but not restricted to) NaCMC, sodium alginate, or other naturally derived anionic polyelectrolytes The preferred anionic polymer is NaCMC, preferably at a concentration of from about 0.05 to about 1.0%. The NaCMC preferably has a molecular weight ranging from about 90,000 to about 250,000 and preferably has a degree of substitution from about 0.65 to about 0.95. The polymer preferably comprises a portion of the formula by weight percent such that the viscosity of the formula does not rise beyond about 10 cps, and imparts a non-syrupy mouth feel to the composition. After the formulation is compounded the final solutions have a pH of from about 5.7 to about 6.5, depending on the degree of substitution, the amount of NaCMC utilized, and the pH of the water used in the formulation. The maintenance of this pH range is important, as it permits the zinc and fluoride to be solubilized together in the same composition and prevents them from precipitating out.

Suitable pharmaceutically acceptable oral hygiene vehicles that may be used alone or in combination with the composition of this invention include glycerol, water, ethanol, polyethylene glycol, propylene glycol, sorbitol, and other compatible vehicles. Preferably, the oral hygiene vehicles are alcohol-free. The formulation may be flavored with various essential oils and flavorants including but not restricted to peppermint oil, spearmint oil, menthol, eugenol, borneol, thymol, methyl salicylate, bornyl acetate, cinnamon oil, cinnamaldehyde, cardamon oil and mixtures thereof. The flavorings can be held in suspension in a microemulsion by alcohol and various non-ionic surfactants including but not restricted to Pluronic TM (a brand of polyoxethylene/polyoxypropylene block copolymers) or Tween TM (a brand of polyoxethylene derivatives of sorbitan fatty acid esters).

The solubilizing system of the present invention relates to the complexing of zinc with sodium gluconate and NaCMC. Although polyvalent cations ordinarily precipitate the NaCMC, there is an excess of gluconate salt present in the formulations of the present invention, which forms a careful balance of ionic charge, preventing the zinc from actively precipitating the NaCMC.

When sodium gluconate alone is used to complex zinc it initially produces clear stable solutions, but upon aging, the zinc begins to destabilize and form cloudy precipitates, most likely attributable to zinc hydroxide or oxychloride and their hydrates. The presence of CMC from the NaCMC in solution acts as a "safety-net" stabilizer, combining with zinc ions that break free from the gluconate complex before they have a chance to form insoluble species. Furthermore, NaCMC acts as a pH buffer, maintaining the solution pH in a range of from 5.5 to 7.0 and preferably in the pH range of from 5.7 to 6.5. These buffer ranges provide for a clear solution.

The compatibility of an anionic polymer such as cellulose gum, e.g., carboxymethylcellulose, with various ionic salts has been extensively studied in the art, and it has been found that the compatibility is largely dependent on the valency of the ionic species. Monovalent cations produce soluble salts, with the viscosity dependent on the order of addition. Polyvalent cations are generally incompatible with CMC, their use to obtain stable, clear solutions is discouraged. It has been unexpectedly found by the present inventors that CMC can be used as a solubilizer for polyvalent zinc. The success of this method is, however, dependent upon the order of addition used during formulation as well as the molecular weight of the CMC itself.

When calculating the quantity of NaCMC in the formulations of the present invention and adjusting for average carboxyl substitution, the zinc ion to carboxyl anion ratio is from about 4:1 to about 15:1 and preferably about 9:1. Clearly then, the majority of zinc ions are not complexed with the CMC, rather the remaining ionic bonds are being occupied by the more prevalent gluconate anion.

EXAMPLES

The present invention will now be illustrated by examples. The examples are not intended to be limiting of the scope of the present invention but read in conjunction with the detailed and general description above, provide further understanding of the present invention and an outline of a process for preparing the compositions of the invention.

The following examples are given to illustrate the invention further, and are not meant to be limitative. In this application all proportions are by weight percent unless otherwise indicated.

EXAMPLE 1

A clear, breath-freshening mouthwash is formulated as follows using the following ingredients:

| Ingredient | w/w % |
| --- | --- |
| Ethyl alcohol, 95% USP | 13.5 |
| Pluronic TM F-127 | 1.2 |
| Tween-80 TM | 0.6 |
| Flavor | 0.4 |
| Sodium Gluconate | 1.5 |
| Sodium CMC | 0.15 |
| Zinc Chloride | 0.25 |
| Sodium Saccharine | 0.5 |
| Glycerin USP | 5.0 |
| Sorbitol, 70% USP | 10.0 |
| Color, d.i. water | q.s. 100.00 |
| pH = 6.2 | |

To approximately 60g of distilled water is added 1.5g of sodium gluconate with stirring. After the gluconate has dissolved, 0.15g of NaCMC is added slowly using a high speed/high shear mixer. The solution is allowed to stir for at least 1 to 2 hours, or until all the CMC grains are dissolved. After the CMC has dissolved, 0.25 g of zinc chloride is added and stirred to dissolution, after which is added the 0.5 g of saccharine, 6.0 g of glycerin and 10.0g of sorbitol solution. This constitutes the aqueous portion of the mouthwash. The greatest stability results from allowing this solution to sit for at least 24 hours after mixing to allow the zinc/CMC complex to form.

The formulation is finished by blending all the remaining ingredients into the alcohol and stirring to dissolution. Then the aqueous portion is added slowly to the alcohol portion with vigorous stirring until the inversion point is reached. This is evidenced by the transition from a pearlescent, translucent fluid to a transparent liquid. After the solution has cleared the remaining aqueous portion may be added.

EXAMPLE 2

An anti-caries, mouth freshening dental rinse of the following composition is formulated as follows:

| Ingredient | w/w % |
| --- | --- |
| Ethyl alcohol, 95% USP | 13.5 |
| Flavor | 0.4 |
| Tween 80 TM | 0.6 |
| Pluronic TM F-127 | 1.2 |
| Sodium Gluconate | 1.5 |
| Sodium CMC | 0.15 |
| Zinc Chloride | 0.25 |
| Sodium Fluoride | 0.023 |
| Sodium Saccharine | 0.75 |
| Glycerin USP | 5.0 |
| Sorbitol, 70% USP | 10.0 |
| Color, d.i. water | q.s. 100.00 |
| pH = 5.9 | |

This formula is prepared according to the method as in Example 1 above, except that the sodium fluoride is added to the aqueous portion following the dissolution of the zinc chloride.

EXAMPLE 3

An anti-tartar dental rinse of the following composition is formulated as follows:

| Ingredient | w/w % |
| --- | --- |
| Ethyl alcohol, 95% USP | 10.0 |
| Pluronic TM F-127 | 0.5 |
| Flavor | 0.6 |
| Sodium Gluconate | 1.5 |
| Sodium CMC | 0.15 |
| Zinc Chloride | 0.50 |
| Sodium Saccharine | 0.05 |
| Magnasweet TM 110 | 1.0 |
| Sorbitol, 70% USP | 10.0 |
| Color, d.i. water | q.s. 100.00 |
| pH = 6.36 | |

This formula is prepared according to the method as in Example 1, above.

In order to illustrate that the composition of the present invention releases a greater quantity of zinc ions from the CMC complex than do the formulations disclosed in U.S. Pat. No. 4,138,477 (represented by Comparative Examples A-B), the following comparative experiment is conducted:

| Formula | Identification |
| --- | --- |
| Example 4 | Zinc Chloride/Na Gluconate/CMC |
| Comparative A | Zinc Chloride/Na Gluconate/Gantrez TM AN-119 (directly substituted for CMC) |
| Comparative B | Zinc Chloride/Gantrez TM AN-119 |

| Ingredient | Example 4 (% w/w) | Comparative Example A (% w/w) | Comparative Example B (% w/w) |
| --- | --- | --- | --- |
| Alcohol Solution | | | |
| EtOH (95%) | 13.5 | 13.5 | 13.5 |
| Anise Oil | 0.05 | 0.05 | 0.05 |
| Menthol | 0.05 | 0.05 | 0.05 |
| Flavor | 0.19 | 0.19 | 0.19 |
| Reodorant | 0.08 | 0.08 | 0.08 |
| Tween TM 80 | 0.6 | 0.6 | 0.6 |
| Poloxamer 407 | 1.2 | 1.2 | 1.2 |
| Aqueous Solution | | | |
| d.i. Water | 52.2 | 52.2 | 52.2 |
| Sodium Gluconate | 1.5 | 1.5 | — |
| Sodium CMC 7M2F | 0.15 | — | — |
| Gantrez TM AN-119 | — | 0.15 | 1.0 |
| Zinc Chloride | 0.25 | 0.25 | 0.25 |
| Sodium Fluoride | 0.023 | 0.023 | 0.023 |
| Sodium Saccharine | 0.1 | 0.1 | 0.1 |
| Sodium Hydroxide (3N) | — | — | 0.1 |
| Glycerin | 5.0 | 5.0 | 5.0 |
| Sorbitol (70%) | 10.0 | 10.0 | 10.0 |
| (di water, color) | (qs 100 ml) | (qs 100 ml) | (qs 100 ml) |
| pH | 5.97 | 4.50 | 5.56 |
| appearance | clear | clear | clear |
| taste | neutral | very tart | tart |
| astringency | moderate | low | low |

An attempt was made to neutralize the comparative A formula with sodium hydroxide, sodium phosphate and ammonium phosphate, however in both cases, the solution developed cloudiness at a pH of from 4.85 to 5.0. It should be noted that the CMC system of the present invention does not require neutralization as the anionic polymer salt acts as a pH buffer.

Then 50 ml each of the above solutions is mixed with 25 ml of 5% calcium chloride in distilled water. The following observations were made:

| Sample ID | Results |
| --- | --- |
| Example 4 | Turbidity, slowly congealing into a gelatinous precipitate (½1 hour) after addition. Cloudy supernatant. |
| Comparative Example A | Slight cloudiness, but no precipitate formed (after 24 hours) |
| Comparative Example B | Immediate viscid precipitate settled out to bottom of flask. Supernatant was clear. |

These observations indicate that Gantrez TM AN-119 directly substituted for the CMC of the formula of the present invention, as shown in Comparative Example A, does not precipitate in the presence of the calcium ion, failing to displace the complexed zinc ion. Therefore in-vivo, the Gantrez TM AN-119 is expected to bind zinc in a similar manner thus rendering the zinc ion unavailable. This strong complexing effect most likely accounts for the lower astringericy of the Gantrez TM system solutions. The resultant samples of precipitate and supernatant are then analyzed for zinc and calcium content, to determine what had been retained or displaced from a quantitative standpoint. The results are as follows:

| Sample ID | Precipitate | Supernatant |
|---|---|---|
| Example 4 | Ca = 19.6% | Not measured |
| | Zn = 1.73% | 0.124% |
| | CMC = 78.6% | Not measured |
| | Mole ratio of calcium/zinc = 18.4/1.0 | |
| Comparative | Ca = 23.3% | Not measured |
| Example B | Zn = 12.2% | 0.044% |
| | AN-119 = 67.5% | Not measured |
| | Mole ratio of calcium/zinc = 4.14/1.0 | |

The results above show that nearly all the zinc was released from Example 4 (the CMC system of the present invention) after calcium treatment. The comparative Gantrez TM system retained nearly 34% of the available zinc. Furthermore, it can be assumed that the lower concentrations of calcium present in the saliva, as compared to that in the experiment above, would have even less effect in displacing the bound zinc.

The formulation of comparative Example A was used to test whether Gantrez TM could be directly substituted for CMC in the formula of the present invention. It can be seen from the results that the initial pH of the Comparative Example A, i.e., 4.5, was too low to be comparable with the pH of the CMC version of the present invention, i.e., 5.9, as represented by Example 4. Further, the solution of Comparative Example A clouded up upon attempted neutralization. These results indicate that Gantrez TM cannot effectively function in the system of the present invention.

Examples 5-8 (Alcohol-Free)

Following the procedure of Example 1 the following formulations were utilized to prepare clear solutions (examples 5, 6 and 8) and a clear gel (Example 7).

| | 5 | 6 | 7 | 8 |
|---|---|---|---|---|
| NaF USP | 0.023 | 0.023 | 0.023 | 0.023 |
| Sodium Saccharine | 0.120 | 0.120 | 0.120 | 0.120 |
| Flavor | 0.375 | 0.375 | 0.375 | 0.375 |
| Tween 80 | 0.600 | 0.600 | 0.600 | 0.600 |
| Alpha Ionone | 0.100 | — | — | — |
| Pluronic F127 | 14.000 | 14.000 | 20.000 | 6.000 |
| Zinc Chloride | 0.25 | 0.25 | 0.25 | 0.25 |
| Sodium Gluconate | 1.50 | 1.50 | 1.50 | 1.50 |
| NaCMC 7M8SF | 0.25 | 0.25 | 0.25 | 0.25 |
| Distilled Water | qs | qs | qs | qs |
| and Color | 100.000 | 100.000 | 100.000 | 100.000 |

Comparative Examples C and D (Alcohol-Free)

Using the formulations provided above for Examples 5–8 but omitting sodium gluconate and NaCMC for Comparative Example C produced an immediate precipitate in the solution and/or gel. Omitting only the NaCMC for Comparative Example D produced hazy (non-clear) solutions and gels which exhibited the formation of fine precipitates when left to stand overnight.

Examples 5-8 utilizing the sodium gluconate and NaCMC in accordance with the invention provided clear alcohol-free zinc salt solutions and gels whereas the Comparative Examples C and D which omitted one or both of these ingredients did not produce clear solutions of zinc salt.

Other objects, features and advantages of the present invention will become apparent from the foregoing detailed description and accompanying examples. It should be understood, however, that the detailed description and specific examples, while indicating embodiments of the invention, are given by way of illustration only, since various changes and modifications within the spirit and scope of the invention will become apparent to those skilled in the art from this detailed description. For example, the zinc compositions of the invention may be provided in a toothpaste or chewing gum product which may provide for the advantageous introduction of bioavailable $Zn^{+2}$ ions into the oral cavity.

Application of the compositions and methods of the present invention for medical and pharmaceutical uses can be accomplished by any clinical, medical and pharmaceutical method and technique as are presently or prospectively known to those skilled in the art. Thus it is intended that the present invention cover the modifications and variations of this invention provided that they come within the scope of the appended claims and their equivalents.

What is claimed is:

1. A stable and clear aqueous composition of a zinc salt comprising a pharmaceutically acceptable zinc salt codissolved with a complexing agent selected from the group consisting of sodium gluconate, maleic acid, aspartic acid, gluconic acid, succinic acid, glucuronic acid, sodium glutamate, fumaric acid and mixtures thereof, in a naturally derived anionic polymer of sodium carboxymethylcellulose or sodium alginate, said composition having a pH of from about 5.7 to about 6.5.

2. The composition of claim 1, wherein said composition is a solution.

3. The composition of claim 1, wherein said composition is a gel.

4. The composition of claim 1, wherein said composition is alcohol-free.

5. The composition of claim 1, wherein said zinc salt is a member selected from the group consisting of zinc chloride, zinc sulfate, zinc acetate, zinc thiocyanate, zinc lactate, zinc salicylate and mixtures thereof.

6. The composition of claim 1, wherein said zinc salt comprises zinc chloride, said complexing agent comprises sodium gluconate, and said naturally derived anionic polymer comprises sodium carboxymethylcellulose.

7. The composition of claim 1, wherein said naturally derived anionic polymer comprises sodium carboxymethylcellulose having a molecular weight ranging from about 90,000 to about 250,000 and a degree of substitution from about 0.65 to about 0.95, in a concentration of from about 0.05 to about 1.0% of the total composition.

8. The composition of claim 1, further comprising a pharmaceutically acceptable oral hygiene vehicle.

9. The composition of claim 8, wherein said selected from the group consisting of glycerol, water, ethanol, polyethylene glycol, propylene glycol, sorbitol, and mixtures thereof.

10. The composition of claim 8, wherein said pharmaceutically acceptable oral hygiene vehicle is alcohol-free.

11. A method for meliorating oral malodor which comprises applying the composition of claim 1 to the oral cavity.

12. The method of claim 11, whereby an effective quantity of bioavailable $Zn^{+2}$ ions are released instantaneously from the composition and absorb onto the oral mucosa and dental pellicle wherein an effective quantity of bioavailable $Zn^{+2}$ ions are released gradually from said composition by an ion-exchange mechanism with salivary $Ca^{+2}$.

13. The method of claim 11, which comprises washing the oral cavity with an aqueous mouthrinse comprising the composition of claim 1.

14. A process for preparing a stable and clear aqueous composition of a pharmaceutically acceptable zinc salt comprising the steps of:
   (a) dissolving a complexing agent in water;
   (b) adding sodium carboxymethylcellulose or sodium alginate to the complexing agent solution of step (a);
   (c) dissolving a pharmaceutically acceptable zinc salt in the solution of step (b); and
   (d) forming a zinc/complexing agent/carboxymethylcellulose or alginate complex in solution.

15. A process for preparing a stable and clear aqueous composition of a zinc salt comprising the steps of:
   (a) dissolving sodium gluconate in water with stirring forming an aqueous gluconate solution;
   (b) adding slowly sodium carboxymethylcellulose to said aqueous gluconate solution with stirring until substantially all the carboxymethylcellulose grains are dissolved;
   (c) thereafter dissolving zinc chloride in the aqueous gluconate carboxymethylcellulose solution with stirring; and
   (d) after mixing, allowing the resultant solution to sit to allow formation of the zinc/gluconate/carboxymethylcellulose complex.

* * * * *

UNITED STATES PATENT AND TRADEMARK OFFICE
CERTIFICATE OF CORRECTION

PATENT NO. : 4,992,259

DATED : February 12, 1991

INVENTOR(S) : Michael T. Schiraldi and Robert K. Denton, Jr.

It is certified that error appears in the above-identified patent and that said Letters Patent is hereby corrected as shown below:

Claim 9, Column 10, line 54, after "wherein said" add
--pharmaceutically acceptable oral hygiene vehicle is a
member --

Signed and Sealed this

Thirteenth Day of April, 1993

Attest:

STEPHEN G. KUNIN

*Attesting Officer*  *Acting Commissioner of Patents and Trademarks*